US006240318B1

(12) United States Patent
Phillips

(10) Patent No.: US 6,240,318 B1
(45) Date of Patent: May 29, 2001

(54) TRANSCUTANEOUS ENERGY TRANSMISSION SYSTEM WITH FULL WAVE CLASS E RECTIFIER

(76) Inventor: Richard P. Phillips, 2688 S. Chadwick St., Salt Lake City, UT (US) 84106

( * ) Notice: Subject to any disclaimer, the term of this patent is extended or adjusted under 35 U.S.C. 154(b) by 0 days.

(21) Appl. No.: 09/427,414

(22) Filed: Oct. 27, 1999

Related U.S. Application Data

(60) Provisional application No. 60/105,785, filed on Oct. 27, 1998.

(51) Int. Cl.[7] .................................................. A61N 1/378
(52) U.S. Cl. .................................................... 607/61
(58) Field of Search .............................. 607/61, 33, 32, 607/30, 27

(56) References Cited

U.S. PATENT DOCUMENTS

| | | |
|---|---|---|
| 4,607,323 | 8/1986 | Sokal et al. . |
| 4,665,896 | 5/1987 | LaForge et al. . |
| 4,679,560 | 7/1987 | Galbraith . |
| 4,685,041 | 8/1987 | Bowman et al. . |
| 4,823,249 | 4/1989 | Garcia, II . |
| 4,891,746 | 1/1990 | Bowman et al. . |
| 5,070,535 | 12/1991 | Hochmair et al. . |
| 5,179,511 | 1/1993 | Troyk et al. . |
| 5,279,292 | 1/1994 | Baumann et al. . |
| 5,350,413 | 9/1994 | Miller . |
| 5,411,537 | 5/1995 | Munshi et al. . |
| 5,613,935 | 3/1997 | Jarvik . |
| 5,630,836 | 5/1997 | Prem et al. . |
| 5,690,693 | 11/1997 | Wang et al. . |
| 5,702,431 | 12/1997 | Wang et al. . |
| 5,713,939 | 2/1998 | Nedungadi et al. . |
| 5,733,313 | 3/1998 | Barreras, Sr. et al. . |
| 5,735,887 | 4/1998 | Barreras, Sr. et al. . |
| 5,755,748 | 5/1998 | Borza . |
| 5,810,015 | 9/1998 | Flaherty . |
| 5,876,425 | 3/1999 | Gord et al. . |

OTHER PUBLICATIONS

Kazimierczuk, M.K. *Class E low dvD/dt rectifier*. Proc. Inst. Elec. Eng., Pt B, Electric Power Appl., vol. 136, pp. 257–262, Nov. 1989.

Kazimierczuk et al. *Resonant Power Converters*, Chapter 4. Wiley–Interscience Publication. New York 1995.

Miller et al. *Development of an Autotuned Transcutaneous Energy Transfer System*. ASAIO Journal. 1993.

Bowman et al. *A New Family of Resonant Rectifier Circuits for High Frequency DC–DC Converter Applications*. IEEE Applied Power Electronics Conference Proceedings. 1998.

Bowman et al. *A Resonant DC–to–DC Converter Operating at 22 Megahertz*. IEEE Applied Power Electronics Conference Proceedings. 1998.

Gutmann, Ronald J. *Application of RF Circuit Design Principles to Distributed Power Converters*. IEEE Transactions on Industrial Electronics and Control Instrumentation, vol. IECI–27, No. 3, Aug. 1980.

Phillips, Richard P. *High Capacity Transcutaneous Energy Transmission System*. ASAIO Journal 1995; 41:000–000.

Reatti, et al. *Class E Full–Wave Low dv/dt Rectifier*. IEEE Transactions on Industrial Electronics and Control Instrumentation. 1992.

Troyk, Phillip R. *Closed–Loop Class E Transcutaneous Power and Data Link for MicroImplants*. IEEE Transactions on Biomedical Engineering, vol. 39. No. 6, Jun. 1992.

*Primary Examiner*—Scott M. Getzow
(74) *Attorney, Agent, or Firm*—TraskBritt

(57) ABSTRACT

A transcutaneous energy transmission system (TETS) including a Class E full wave low dv/dt rectifier in the implantable receiver circuit. The TETS provides power for any kind of implantable device requiring a source of DC power for operation. The Class E full wave low dv/dt rectifier provides efficient conversion of radio frequency power to direct current power. Another embodiment of a TETS includes a Class E full wave low dv/dt rectifier with circuitry for synchronous rectification. A receiver circuit including a Class E full wave low dv/dt rectifier configured for use with a transmitter circuit is also disclosed.

20 Claims, 7 Drawing Sheets

TRANSCUTANEOUS ENERGY TRANSMISSION SYSTEM WITH FULL WAVE CLASS E RECTIFIER

CROSS-REFERENCE TO RELATED APPLICATION

This utility patent application claims the benefit of Provisional Patent Application Ser. No. 60/105,785, titled TRANSCUTANEOUS ENERGY TRANSMISSION SYSTEM WITH FULL WAVE CLASS E RECTIFIER, filed Oct. 27, 1998.

BACKGROUND OF THE INVENTION

1. Technical Field

This invention relates generally to transcutaneous energy transmissions systems. In particular, the invention relates to the use of two coils to inductively transmit radio frequency power across an intact skin boundary for use by a device implanted under the skin, or otherwise within the body of, a living being.

2. State of the Art

Transcutaneous energy transfer systems (TETS) have been used to provide power for a number of implanted devices such as: low power prosthetic devices; cochlear implants, muscle stimulators, bone growth stimulators and stimulators of the visual cortex, and higher power devices; total artificial hearts, and ventricular assist devices. The inductively coupled coils of a TETS, one implanted under the skin, the other resting on the surface of the skin, permit electrical interaction between the implanted device and external circuits through intact skin, and bring about the transfer of power from the external circuit to the internal circuit avoiding penetration of the skin by electrical conductors. FIG. 1 illustrates a vertical cross section through an exemplary prior art TETS as implanted and in position for use.

The interaction between the coils requires alternating current; usually a frequency between 100 kHz and 1 MHz is chosen. In order to improve the efficiency with which power is delivered, the coils are incorporated into either series or parallel resonant circuits by connecting them to capacitors. The resonant circuits can be tuned with a natural resonant frequency less than, equal to, or greater than the operating frequency, as described by the U.S. Pat. Nos. 4,441,210 and 5,070,535 to Hochmair et al. and U.S. Pat. No. 4,679,560 to Galbraith. In the following discussion, the efficiency with which power is transferred to the internal coil will be referred to as link efficiency. This quantity is related to the overall efficiency of the TETS by the expression:

$$\eta_{overall} = (\eta_{DC\ to\ RF})(\eta_{link})(\eta_{RF\ to\ DC}) \tag{1}$$

Thus, the overall efficiency is equal to the product of three sequential process efficiencies.

DC to RF Conversion

LaForge in U.S. Pat. No. 4,665,896 and Miller in U.S. Pat. No. 5,350,413 describe the need to have an active control circuit to adjust the frequency of the circuitry driving the external resonant circuit such that a constant phase relationship is maintained between the drive voltage and the resonant current. With this "auto-tuning" circuit, as described by LaForge and Miller, the frequency of operation is maintained at, or near, the resonant frequency. Because of variable coupling between the transmitter and receiver coils, the resonant frequency is a function of relative coil position.

Link Efficiency

In U.S. Pat. No. 4,441,210 to Hochmair et al., resonant frequencies of both the external and the internal circuits were implicitly tuned to the operating frequency. Hochlmair et al. explicitly clarified this point in his U.S. Pat. No. 5,070,535. Hochmair et al. adjusted the quality factor, Q, of his circuits in order to achieve critical coupling and an output that was not sensitive to the relative position of the coils. The degree of coupling is indicated by the coupling coefficient, k, which is equal to unity for an ideal transformer and equal to zero for isolated coils. For given values of $Q_R$ and $Q_T$ in the external and internal circuits, there is a value of the coupling coefficient at which the coupling is critical, that is, the output is then a maximum. Critical coupling is achieved when $$k^2 = \frac{1}{Q_R Q_T} \tag{2}$$

By adjusting the Q values, the output can be made to have its maximum at the value of k corresponding to the coil separation expected when the system is actually used. A by-product of the Q tuning approach is that the link efficiency of a TETS would be a maximum of 50% when operated at critical tuning.

Galbraith, U.S. Pat. No. 4,679,560, explored the operation of a TETS with resonant frequencies varying from the operating frequency. Galbraith used frequency modulation to communicate digital information to a cochlear implant to which a TETS was connected. Setting the resonant frequencies above and below the center frequency, in what he called "stagger tuning," increased the range of signal transmission frequency over which the system could operate. Galbraith studied the variation in the voltage gain of a TETS with coupling coefficient, k, and found that stagger tuning permitted the gain to be substantially unchanged within a range of frequencies and coupling coefficient. Galbraith also pointed out that, by designing high values of Q and tuning the external circuit to resonate below the operating frequency, an overall efficiency of greater than 50% was possible while maintaining insensitivity to variation in relative coil position.

Hochmair et al., in U.S. Pat. No. 5,070,535, discloses improved efficiency while maintaining insensitivity to relative coil position brought about by detuning the transmitter resonant frequency. In other words, Hochmair et al. set the resonant frequency of the transmitter different from the operating frequency, while the receiver resonant frequency was equal to the operating frequency.

RF to DC Conversion

Current produced in an internal coil of a TETS alternates polarity at the frequency of operation. However, implanted devices require a supply of direct current. A rectifier is typically used in a TETS to convert alternating current to direct current. There are many types of rectifiers. The most common rectifier used in a TETS is a bridge type full wave rectifier. Other conventional TETS use a center tapped rectifier. Exemplary bridge type full wave rectifiers may be found in U.S. Pat. Nos. 3,867,950, 3,942,535, 4,187,854, 5,350,413, 5,702,431, 5,713,939, 5,735,887 and 5,733,313. Exemplary center tapped rectifiers may be found in U.S. Patent Nos. 3,454,012, 4,082,097, 4,096,866 and 4,665,896. Rectifiers differ in efficiency. The ratio of DC current output by the rectifier to the AC current input into the rectifier is characterized by the conversion coefficient $K_i$. Table 1 below, lists values of $K_i$ for a number of current driven rectifier circuits.

TABLE 1

AC to DC conversion ratios for Class D (bridge) rectifiers.

| Current Driven Rectifier Type | AC to DC Conversion Coefficient, $K_i$ |
|---|---|
| Class D half wave | 0.45 |
| Class D transformer center tapped | 0.90 |
| Class D full wave bridge | 0.90 |

A rectifier may be considered current driven if the resonant circuit to which it is connected has a quality factor, Q, greater than three, where the load is a resistor.

However, Class D rectifiers have an undesirable ringing problem as described by Bowman et al. in U.S. Pat. No. 4,685,041. In bridge rectifiers, the diodes which are not conducting at some instant are contributing reverse bias capacitance to the circuit which, in combination with parasitic inductance in the connections among the components, promotes ringing. Bowman et al. suggested that these parasitic circuit elements be considered and utilized, if possible, in rectifiers for use at high frequencies. R. J. Gutmann, *Application of RF Circuit Design Principles to Distributed Power Converters,* IEEE Transactions Industrial Electronics, Control, and Instrumentation, Vol. IECI-27, pp. 156–64, (1980), discloses a rectifier design using LC filters to control the ringing problem.

Miller, in U.S. Pat. No. 5,350,413, discloses a full bridge rectifier with a capacitor across the input to the rectifier for the purpose of maintaining a high quality factor, Q, of the receiver resonant circuit when the implant presented a high resistance at light load. As disclosed in Miller, AC current flows through the capacitor during all load conditions and increased the RF current flowing in the receiver coil, but did not contribute to the DC output current.

FIG. 2 is a circuit diagram of a Class E half wave low dv/dt rectifier with a parallel capacitor as disclosed in the prior art. As shown in FIG. 2, the Class E half wave low dv/dt rectifier includes a diode, D, a shunt capacitor, C, a filter capacitor, $C_f$, and a filter inductor $L_f$. Load resistor, $R_L$, is used to model the load of an implantable device 26 (shown in FIG. 3 in the context of the present invention). The shunt capacitor, C, controls the diode voltage when the diode, D, is not conducting. Filter capacitor, $C_f$ and the load resistance, $R_L$, act as a first-order low pass output filter.

A full wave Class E rectifier has a high AC to DC current conversion ratio. Because of this high current conversion ratio, the current that circulates in the internal coil is reduced and heating due to resistance in the internal coil is reduced in proportion to the second power of the circulating current. Table 2, below, lists the conversion ratio of AC input current to DC output current, $K_i$, for Class E low dv/dt rectifiers assuming lossless diodes, perfect conductors (other than the load resistance) and the AC power delivered to the rectifier is equal to the DC power delivered to the load.

TABLE 2

AC Current to DC Current Conversion Ratios for Class E Rectifiers

| Rectifier Type | Conversion Ratio, $K_i$ |
|---|---|
| Class E half wave | 0.7595 |
| Class E full wave | 1.519 |

The full wave Class E rectifier also features an essentially sinusoidal current and voltage at its terminals for reduced electromagnetic interference (EMI) and compatibility with a resonant receiver design. The input resistance of the full wave Class E rectifier has a maximum at an intermediate load. The quality factor for the resonant receiver circuit does not fall below a threshold value even as the load resistance increases. The input capacitance of the full wave Class E rectifier changes by a factor of five as the power output changes from maximum to zero. However, this change in input capacitance alters the resonant frequency of the receiver and reduces link efficiency.

Autotuning

LaForge, in U.S. Pat. No. 4,665,896, discloses an inductive power supply for body implant which utilizes a "belt skin transformer." LaForge discloses a transmitter coil current sensing circuit and phase lock loop that generate switch control signals for a half bridge transmitter coil driver. This circuit adjusts driver frequency depending on the resonant condition sensed and automatically adjusts the level of power delivered to the transmitter coil. Miller et al., *Development of an Autotuned Transcutaneous Energy Transfer System,* ASAIO JOURNAL, (1993), discloses a phase locked loop circuit which changed switch frequency in order to maintain transmitter and receiver at resonance, while varying the coupling coefficient.

However, there remains a need in the art for a transcutaneous energy transmission system which operates efficiently at frequencies above 500 kHz with light weight coils and reduces heat generation in the internal coil for improved patient comfort and biocompatability.

SUMMARY OF THE INVENTION

The inventive TETS disclosed herein improves upon the efficiency of prior art systems and compatibility with body tissue by reducing the amount of heat produced by parts of the system implanted within a body. The efficiency of the inventive TETS is substantially continuously maintained at a high level even though both the coefficient of coupling between the coils, and power required by the implant, vary. The invention operates at frequencies above 500 kHz and enables the coils to be small and lightweight also enhancing compatibility and patient convenience.

There are several advantageous results of using the Class E full wave low dv/dt rectifier in the TETS according to the invention The link efficiency can be maintained at a high level at all load conditions presented by the implanted device. The losses in the receiver coil are reduced due to the high AC to DC current conversion ratio of the rectifier. The losses in the rectifier due to the forward voltage drop of the diodes there is cut in half compared to a full bridge rectifier. The current and voltage at the rectifier input terminals are moderately distorted sinusoidal waveforms with no significant power lost in harmonics. The transmitter can be maintained in a "soft switching" condition for reduced switching losses.

BRIEF DESCRIPTION OF THE DRAWING FIGURES

In the drawings, which illustrate what is currently regarded as the best mode for carrying out the invention and in which like reference numerals refer to like parts in different views or embodiments:

DETAILED DESCRIPTION OF THE INVENTION

Figure 1:
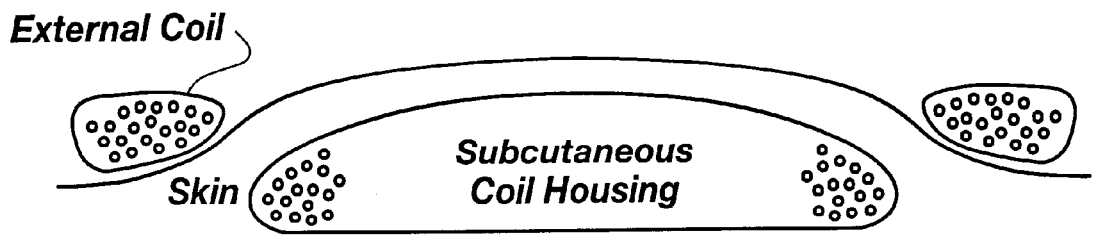
FIG. 1 is a vertical cross section through a prior art TETS as implanted and in position for use.
Figure 2:
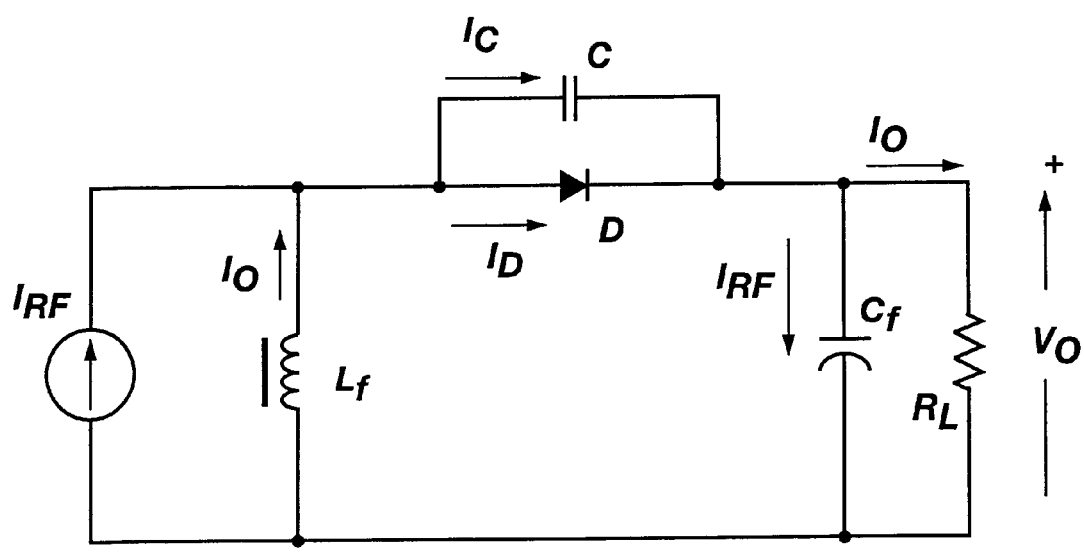
FIG. 2 is a circuit diagram of a Class E half wave low dv/dt rectifier with a parallel capacitor as disclosed in prior art.
Figure 3:
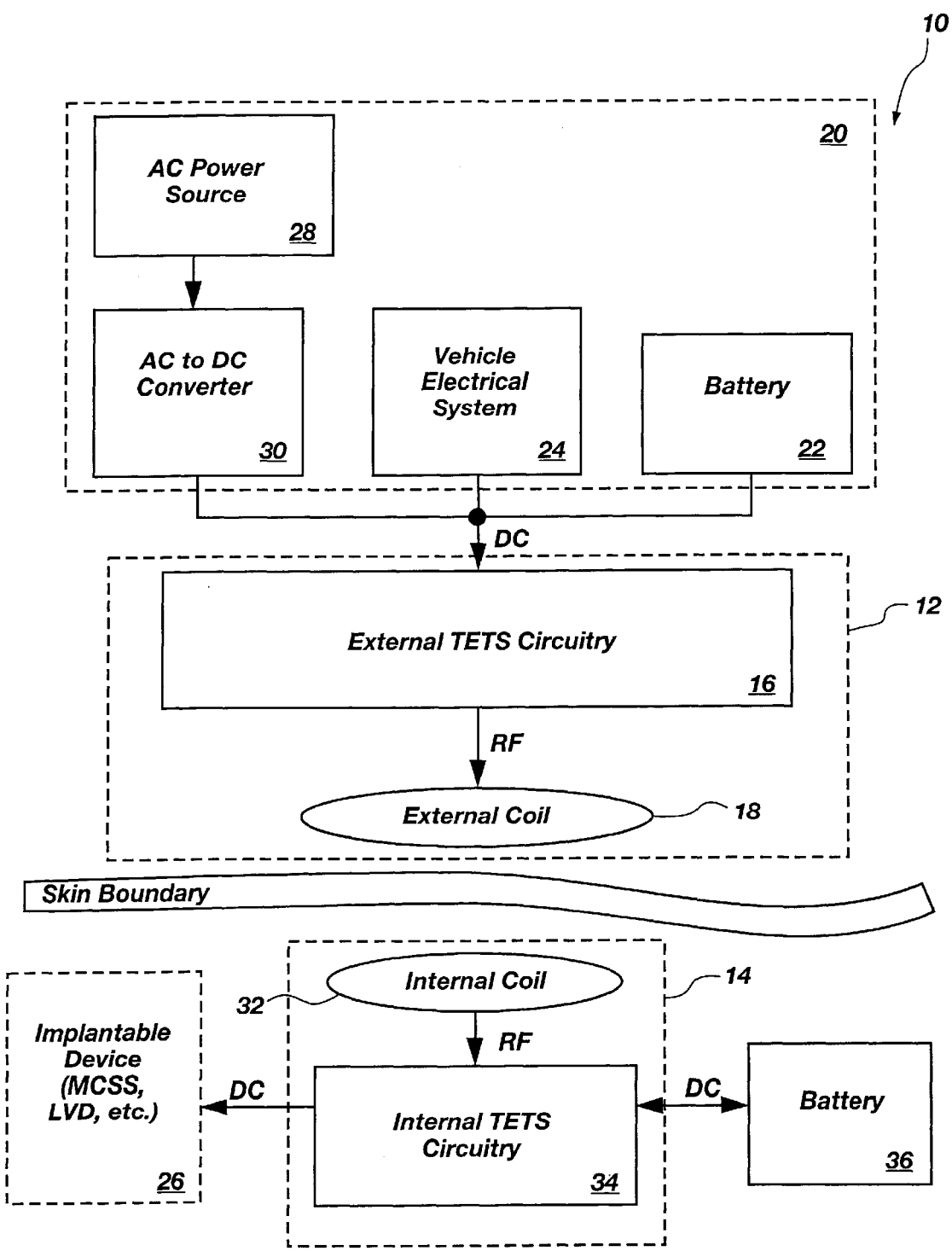
FIG. 3 is a block diagram of a TETS system in accordance with the invention.

FIG. 3 shows a block diagram of a transcutaneous energy transmission system (TETS) 10 according to the invention for powering an implantable device 26. The implantable device 26 may be a mechanical circulatory support system (MCSS), a left ventricular device (LVD), a muscle stimulator, vision prosthesis, audio prosthesis or other implantable device requiring DC electrical power for operation. The TETS 10 includes a transmitter circuit 12 to be placed externally of the body proximate an implantable resonant receiver circuit 14. The terms "implantable resonant receiver circuit","resonant receiver circuit" and "receiver circuit" are used interchangeably herein. The transmitter circuit 12 includes external TETS circuitry 16 and an external coil 18. The external TETS circuitry may comprise a Class D amplifier to drive external coil 18. External coil 18 may comprise Litz wire to minimize the skin effect, as is known to one of skill in the art. The external TETS circuitry 16 requires a DC power source 20 for operation. The DC power source 20 may be a battery 22, which may be rechargeable. Battery 22 may comprise any battery technology, including but not limited to, lithium ion, nickel metal hydride, nickel cadmium and alkaline sufficient to power, or charge the battery of, an implanted device 26. Battery 22 provides patient mobility for extended periods of time. Battery 22 may be integrated with the transmitter circuit 12. The DC power source 20 may be a vehicle electrical system 24. A vehicle electrical system 24 may be used to power a TETS 10 and/or charge an integrated or attached battery 22. The DC power source 20 may also be an AC power source 28 with an AC to DC power converter 30.

The implantable receiver circuit 14 includes an internal coil 32 and internal TETS circuitry 34 for converting RF energy into DC electrical power for an implantable device 26. Internal coil 32 may comprise Litz wire to minimize the skin effect as is known to one of skill in the art. The implantable receiver circuit 14 is electrically coupled to the implantable device 26 and to an implantable battery 36. Implantable battery 36 is rechargeable and may comprise any battery technology, including but not limited to, lithium ion, nickel metal hydride, nickel cadmium and alkaline sufficient to power an implanted device 26. Implantable battery 36 provides patient mobility for short periods of time. Implantable battery 36 may be integrated with the implantable receiver circuit 14.

Figure 4:
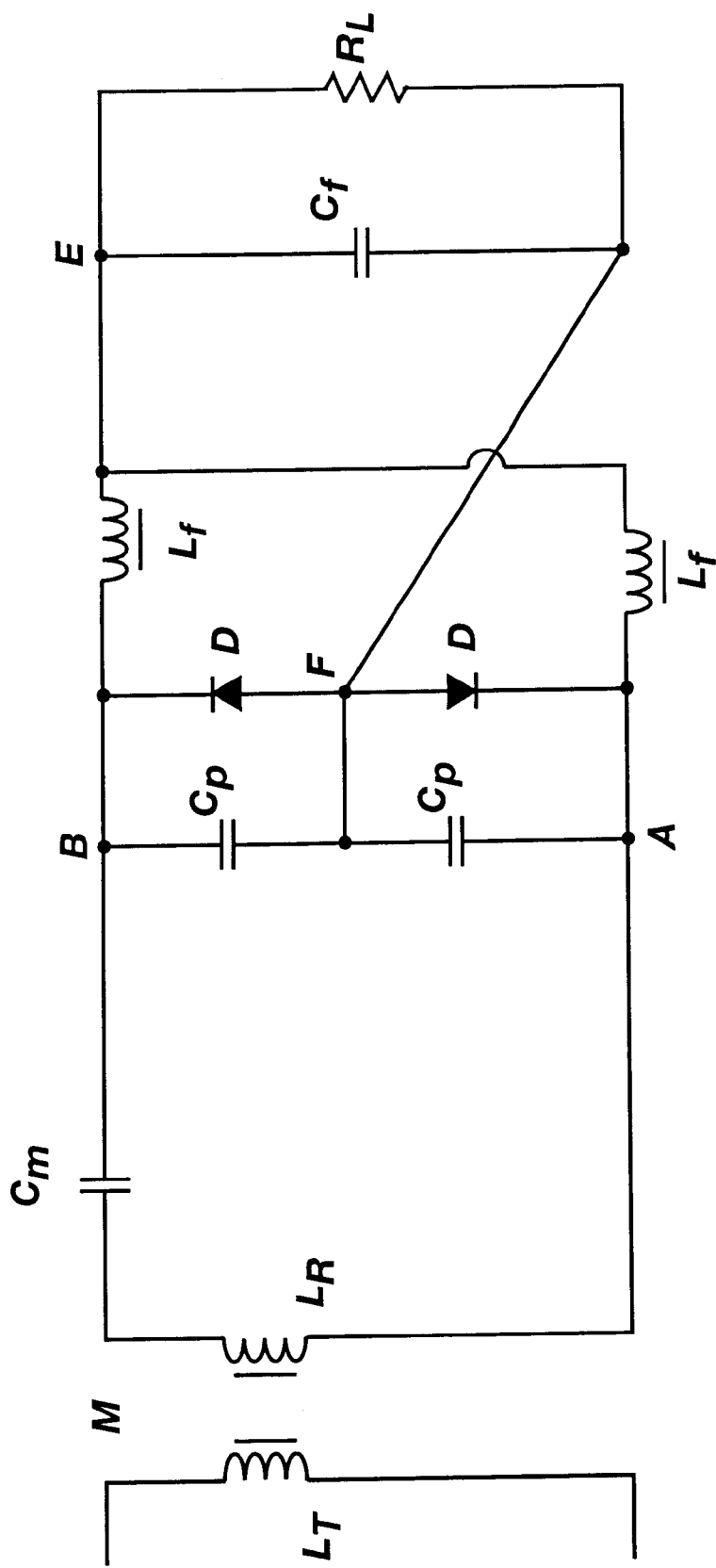
FIG. 4 is a circuit diagram of a Class E full wave low dv/dt rectifier and an equivalent simulation model in accordance with the invention.

Internal TETS circuitry 34 includes a Class E full wave low dv/dt rectifier, see FIG. 4. The terms "Class E full wave low dv/dt rectifier" and "Class E full wave rectifier" are used interchangeably herein. The variation in input capacitance which reduces link efficiency noted above has been overcome with frequency tracking. By using frequency tracking, high efficiency at all loads may be achieved. The Class E full wave rectifier has been incorporated into a resonant receiver circuit in a novel way. The theory developed by Galbraith has been extended to provide quantitative expressions that describe the link efficiency, $\theta_{link}$. Additionally, the relative phase of the voltage and current in the implantable receiver circuit 14 has been related to the phase in the transmitter circuit 12.

The Class E full wave rectifier of the invention reduces heating in the internal coil 32, relative to a Class D full wave bridge rectifier. A transformer may also be used in conjunction with a Class E full wave rectifier to further reduce current in the internal coil 32.

Referring to FIG. 4, a circuit diagram of receiver circuit with a Class E full wave low dv/dt rectifier is shown. The internal coil (32 in FIG. 3) is modeled as $L_R$ with a first end of the inductor tied to node A. A series matching capacitance, $C_m$, has a first end coupled to the second end of $L_R$ and second end coupled to node B. $C_m$ is selected to achieve a resonant frequency of operation. Two diodes, D, with anodes coupled at node C and cathodes coupled to nodes A and B. Two parallel capacitors, $C_p$, are placed in series between nodes A and B and in parallel with each diode, D. The node common to the parallel capacitors, $C_p$, is tied to the common anode of the diodes and is referred to as node F. A first inductance, $L_f$, is coupled between node B and output node E. A second inductance, $L_f$, is coupled between node A and output node E. A filter capacitor, $C_f$, is coupled between output node E and node F. The load resistor, $R_L$, is coupled parallel to filter capacitor, $C_f$, and represents the resistance of the implantable device (26 of FIG. 3).

For a given power requirement, $P_o$, output voltage, $V_o$, and operating frequency, f, the components of an Class E full wave low dv/dt rectifier may be selected. The load resistance, $R_L$, may be calculated from the following equation:

$$R_L = \left( \frac{V_o^2}{P_o} \right) \tag{3}$$

where $R_L$ is measured in Ohms ($\Omega$). Peak output current, $I_L$, passing through the load resistance, $R_L$, can be calculated from the following equation (Ohm's Law):

$$I_L = \frac{V_o}{R_L} \tag{4}$$

where $I_L$ is measured in Amperes (A). From the operating frequency, f, we can calculate the angular frequency, $\omega$, from the following equation:

$$\omega = 2\pi f \tag{5}$$

where $\omega$ is measured in radians per second (Rad/s).

The duty cycle, D, for the Class E full wave low dv/dt rectifier should not exceed 0.5. When the D>0.5, both diodes are conducting simultaneously, and the implantable receiver circuit (14 of FIG. 3) is not resonant. Additionally, when D>0.5, the TETS will suffer losses in the link efficiency, $\theta_{link}$, and losses in the AC to DC conversion in the Class E full wave low dv/dt rectifier itself. It is preferable to operate the Class E full wave low dv/dt rectifier at D=0.5. The parallel capacitance, $C_p$, can be calculated from the following equation:

$$C_p = \frac{1}{2\pi\omega R_L} \quad (6)$$

where $C_p$ is measured in Farads (F).

The behavior of the Class E full wave low dv/dt rectifier may be modeled as an equivalent capacitance, $C_{Eq}$, in series with an equivalent resistance, $R_{Eq}$. When D=0, the Class E full wave low dv/dt rectifier does not shunt either capacitor with the result that the equivalent capacitance of the rectifier in the implantable receiver circuit equals half the parallel capacitance. When D<0.5, both parallel capacitors appear in series in the Class E full wave low dv/dt rectifier. As the duty cycle increases, the equivalent capacitance increases until, at D=0.5, the Class E full wave low dv/dt rectifier shunts one of the two parallel capacitors, $C_p$, at all times. This phenomenon gives rise to the need for the operating frequency of the TETS to increase as the load resistance increases in order to maintain the efficiency of power delivery.

When D=0.5 the conversion ratio, $K_i$, of the DC output current, $I_L$, to the root mean squared (rms) AC input current, $I_{AC,in}$ is, $K_i=1.519$. Given $K_i=1.519$ and the DC output load current, $I_L$, the AC input current, $I_{AC,in}$ may be calculated from the following equation:

$$I_{AC,in} = \frac{I_L}{1.519} \quad (7)$$

where $I_{AC,in}$ is measured in rms A. The equivalent resistance, $R_{Eq}$, may be calculated from the following equation:

$$R_{Eq} = \frac{P_o}{\left(\frac{I_L}{1.519}\right)^2} \quad (8)$$

where $R_{Eq}$ is measured in Ω. A mathematical analysis of the rectifier for D=0.5 shows that $C_{Eq} > C_p$. The equivalent capacitance, $C_{Eq}$, may be calculated from the following equation:

$$C_{Eq} = 2.36 \cdot C_p \quad (9)$$

An illustrative example for selecting component values for the Class E full wave low dv/dt rectifier follows. Suppose the required output power, $P_o$, of the implantable device is 50 Watts (W), the required output voltage, $V_o$, is 15 Volts (V), the operating frequency,f, is 500 kHz with a duty cycle, D, of 0.5. From Eq. 3, $R_L=4.5$ Ω. With this value of $R_L$, the peak output current may be calculated, $I_L=3.3$ A, from Eq. 4. The angular frequency, $\omega=3.14\times10^6$ Rad/s, from Eq. 5. The parallel capacitance, $C_p=11.3$ nF, using Eq. 6. Using Eqs. 7–9 and the given duty cycle, D, the equivalent series capacitance and resistance of the Class E full wave low dv/dt rectifier may be calculated as $C_p=11.3$ nF, $C_{Eq}=26.6$ nF and $R_{Eq}=10.4$ Ω.

The link efficiency, $\theta_{link}$, may be calculated from the following equation:

$$\eta_{link} = \frac{k^2}{k^2 + \frac{1}{Q_T Q_R}} \quad (10)$$

where $\theta_{link}$ is a number between 0 and 1 and k is the coupling coefficient as indicated in Eq. 2. The quality factor of the implantable receiver circuit, $Q_R$, must be selected to achieve a given link efficiency, $\theta_{link}$. Eq. 10 may be solved for $Q_R$:

$$Q_R = \frac{1}{Q_T\left(\frac{k^2}{\eta_{link}} - k^2\right)} \quad (11)$$

An illustrative example for selecting the quality factor for the implantable receiver circuit follows. Suppose the quality factor for the transmitter circuit, $Q_T=150$, the coupling coefficient between the external coil and the internal coil, k=0.18 and the link efficiency, $\theta_{link}=0.95$. The coupling From Eq. 11, the quality factor of the implantable receiver circuit is, $Q_R=3.9$.

The internal coil inductance may be calculated from the expression for the quality factor for the implantable receiver circuit:

$$Q_R = \frac{\omega L_R}{R_{Eq}} \quad (12)$$

Solving for $L_R$, $$L_R = \frac{Q_R R_{Eq}}{\omega} \quad (13)$$

where $L_R$ is measured in Henries (H). Continuing with the numerical example above, using Eq. 13, $L_R=12.9$ μH.

Finally, it is desirable to select a matching capacitance, $C_m$, to be place in series with the internal coil inductance and the Class E full wave low dv/dt rectifier to operate the implantable receiver circuit at resonance. The resonant angular frequency may be calculated from the following equation:

$$\omega = \frac{1}{\sqrt{L_R C_R}} \quad (14)$$

where $C_R$ is the capacitance of the implantable receiver circuit. Solving for $C_R$:

$$C_R = \frac{1}{\omega^2 L_R} = \frac{1}{\frac{1}{C_{Eq}} + \frac{1}{C_m}} \quad (15)$$

where $C_R$ is measured in F. Again continuing with the numerical example, $C_R=7.8$ nF. From Eq. 15 an expression for the matching capacitance, $C_m$, may be derived:

$$C_m = \frac{1}{\frac{1}{C_R} - \frac{1}{C_{Eq}}} \quad (16)$$

where $C_m$ is measured in F. Using Eq. 16 with $C_R=7.8$ nF and $C_{Eq}=26.6$ nF, $C_m=11.1$ nF.

Figure 5:
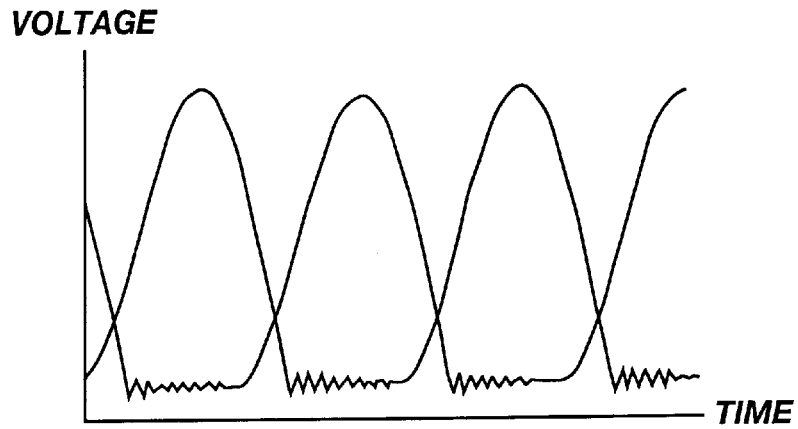
FIG. 5 is a graph of actual voltage waveforms from a digital oscilloscope appearing at the diode cathodes of the circuit in FIG. 4 in accordance with the invention.

FIG. 5 is a graph of actual voltage waveforms from a digital oscilloscope appearing at the diode cathodes of the circuit in FIG. 4 in accordance with the invention.

Figure 6:
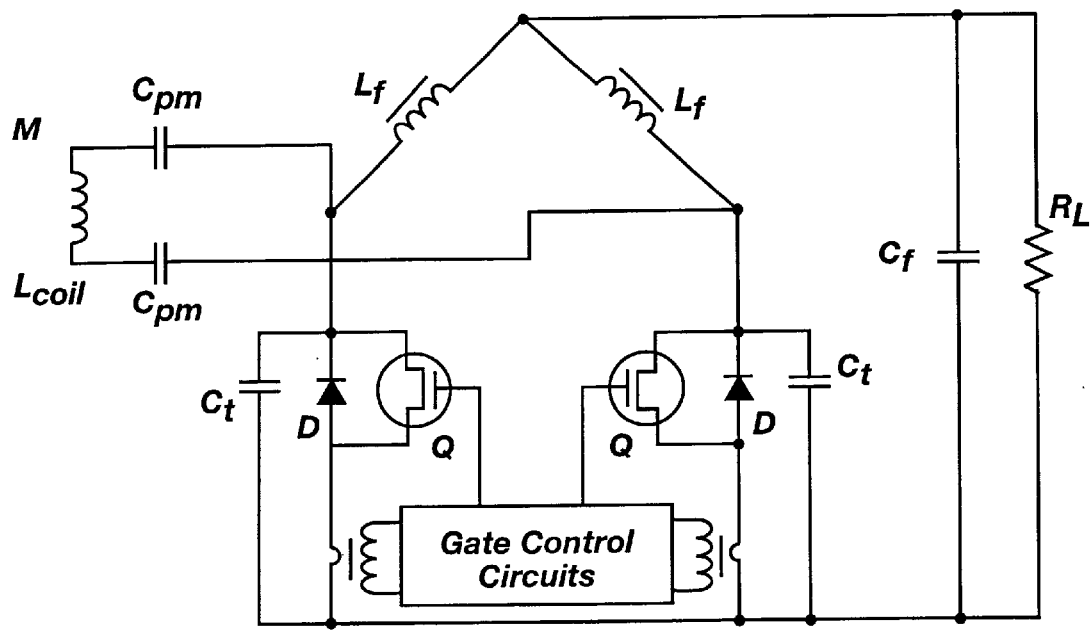
FIG. 6 is a circuit diagram of a receiver circuit with a Class E full wave low dv/dt rectifier and additional gating circuitry in accordance with the invention.

FIG. 6 illustrates a circuit diagram of an implantable receiver circuit with a Class E full wave low dv/dt rectifier and additional gating circuitry in accordance with the invention. The additional gating circuitry and field effect transistors (FETs) provide synchronous rectification to reduce diode losses. The function of the gating circuitry is to sense current flowing in the diodes and to turn on the transistors when the current in the diodes is above a threshold current. The gate control circuitry may comprise a one turn primary or a current sensing resistor or other means of sensing current. The design of gate control circuitry is within the knowledge of one of skill in the art.

Figure 7:
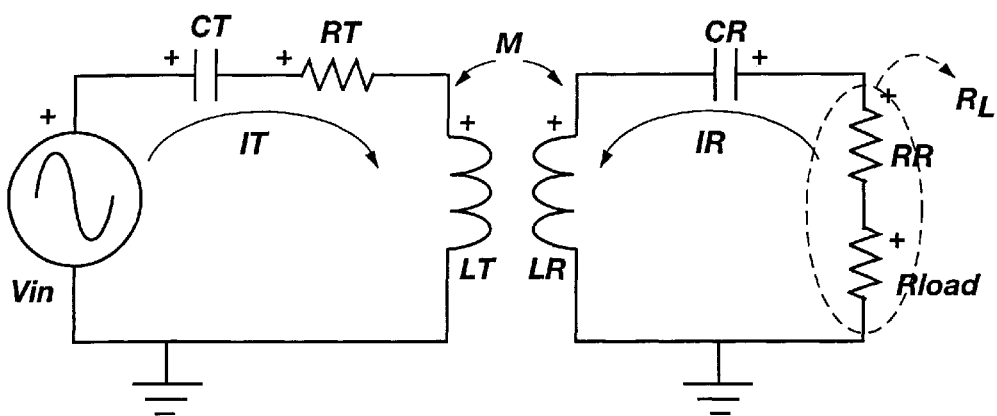
FIG. 7 is a model circuit diagram of series resonant circuits in accordance with the invention.
Figure 8A:
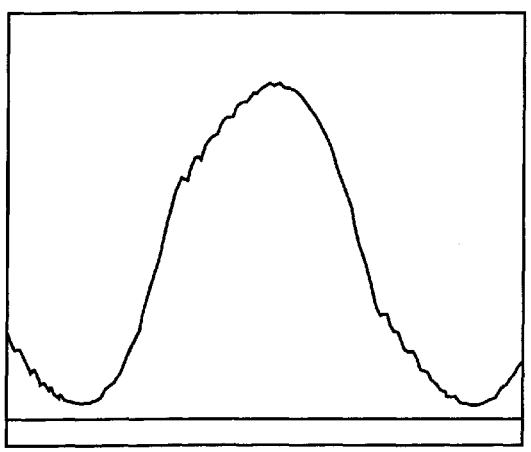
FIGS. 8A and 8B are actual and predicted waveforms of the output the circuit of FIG. 7 in accordance with the invention.
Figure 8B:
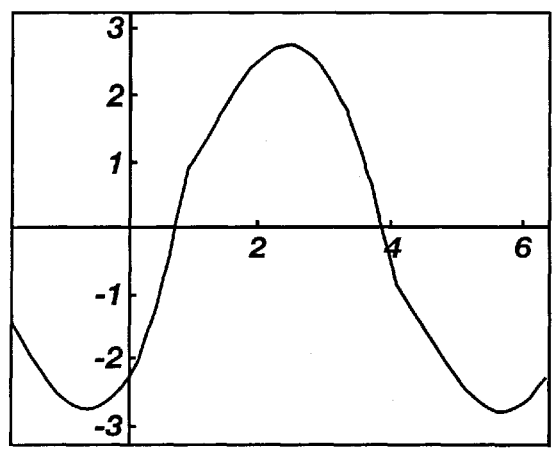
Figure 9:
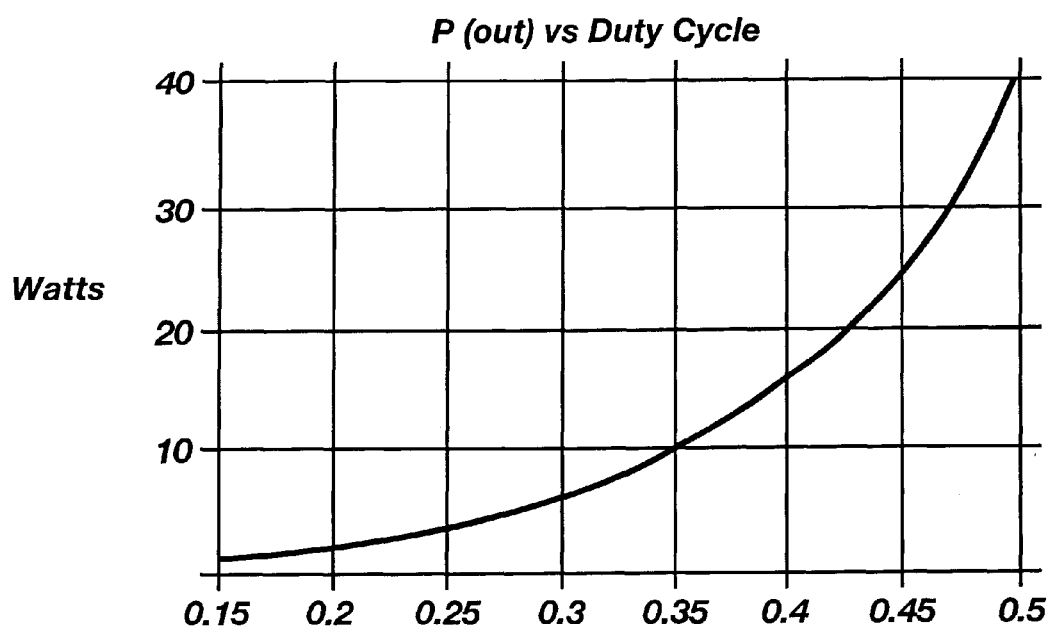
FIG. 9 is a graph of output power versus duty cycle for a TETS Class E full wave rectifier in accordance with the invention.
Figure 10:
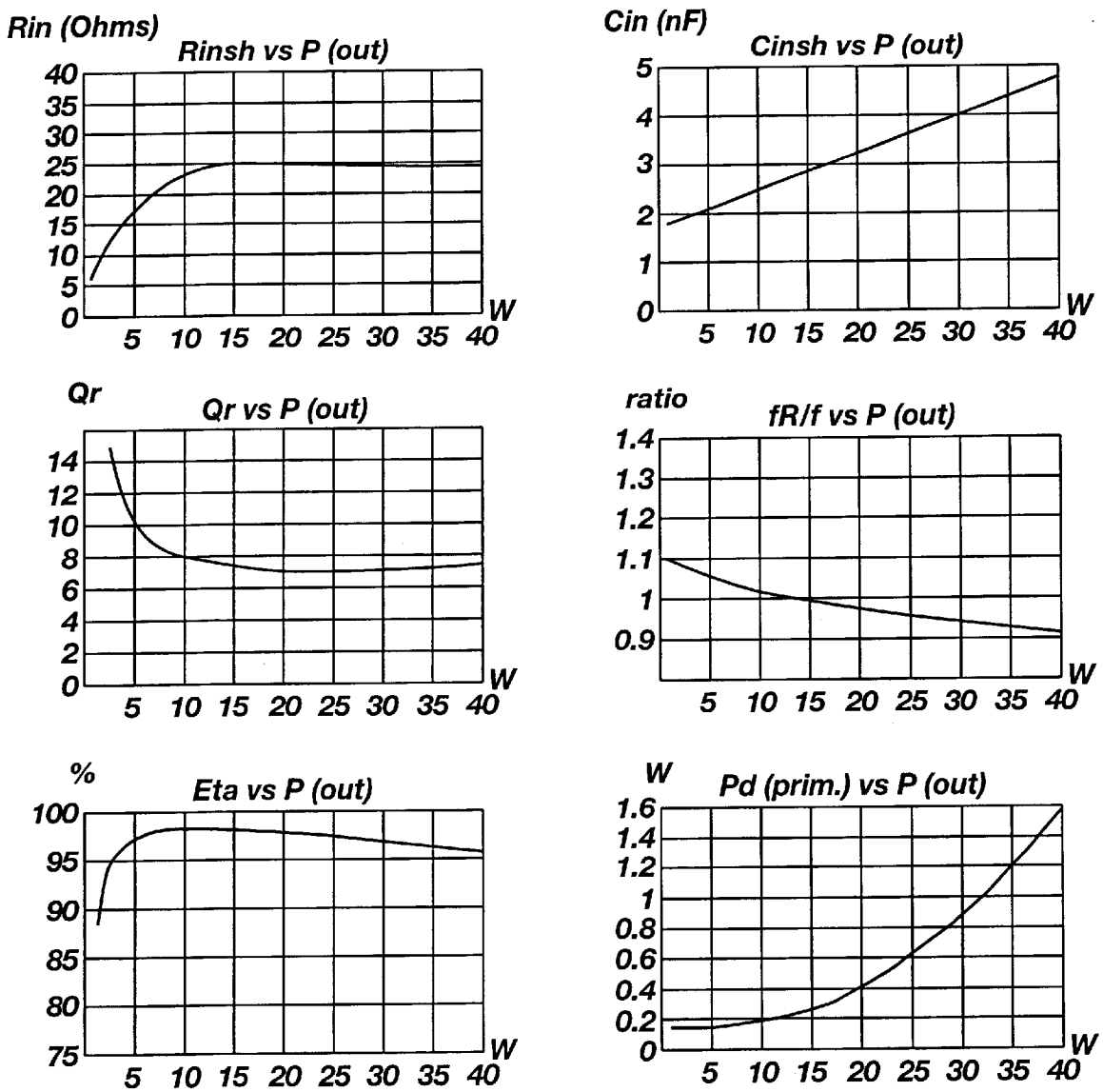
FIG. 10 illustrates graphical results from the analytic model of the inductive link and the Class E full wave low dv/dt rectifier in accordance with the invention.

FIG. 7 is a model circuit diagram of series resonant circuits in accordance with the invention which may be used to model a TETS. FIGS. 8A and 8B are, respectively, actual and predicted waveforms of the output the circuit of FIG. 7 in accordance with the invention. FIG. 9 is a graph of output power versus duty cycle for a TETS Class E full wave rectifier in accordance with the invention. FIG. 10 illustrates graphical results from the analytic model of the inductive link and the Class E full wave low dv/dt rectifier in accordance with the invention.

Although this invention has been described with reference to particular embodiments, the invention is not limited to these described embodiments. Rather, it should be understood that the embodiments described herein are merely exemplary and that a person skilled in the art may make many variations and modifications without departing from the spirit and scope of the invention. All such variations and modifications are intended to be included within the scope of the invention as defined in the appended claims.

What is claimed is:

1. A transcutaneous energy transmission system (TETS) comprising:
   a transmitter circuit for generating a radio frequency (RF) signal; and
   an implantable receiver circuit for inductively coupling with said transmitter circuit, wherein said receiver circuit includes a Class E full wave low dv/dt rectifier.

2. The TETS of claim 1, wherein said transmitter circuit comprises:
   external TETS circuitry for receiving a DC power input and outputting said RF signal; and
   an external coil electrically coupled to said external TETS circuitry for receiving said RF signal and generating an electromagnetic field responsive thereto.

3. The TETS of claim 2, wherein said external TETS circuitry comprises a Class D amplifier circuit.

4. The TETS of claim 2, wherein said external coil comprises Litz wire.

5. The TETS of claim 1, wherein said implantable receiver circuit comprises:
   an internal coil for receiving said RF signal;
   a capacitor in series with said internal coil selected to provide a resonant condition in said implantable receiver circuit; and
   a Class E full wave low dv/dt rectifier coupled to said internal coil and said capacitor for rectifying said RF signal.

6. The TETS of claim 1, wherein said implantable receiver circuit includes a rechargeable battery.

7. The TETS of claim 1, further comprising a DC power source for generating said DC power input to said external TETS circuitry.

8. The TETS of claim 7, wherein said DC power source is an AC power source coupled to an AC to DC converter.

9. The TETS of claim 7, wherein said DC power source is a vehicle electrical system.

10. The TETS of claim 7, wherein said DC power source is a battery.

11. The TETS of claim 10, wherein said battery is selected from the group consisting of lithium ion, nickel metal hydride, nickel cadmium and alkaline.

12. The TETS of claim 10, wherein said battery is rechargeable.

13. The TETS of claim 1, further comprising an implantable device electrically coupled to and powered by said implantable receiver circuit.

14. The TETS of claim 13, wherein said implantable device is a mechanical circulatory support system.

15. The TETS of claim 13, wherein said implantable device is a left ventricular device.

16. An implantable receiver circuit for inductively coupling to an external transmitter circuit, said implantable receiver circuit configured for powering an implantable device and comprising:
   an inductive coil for generating an RF signal responsive to an electromagnetic field generated by the external transmitter circuit;
   a capacitor in series with said inductive coil; and
   a Class E full wave low dv/dt rectifier coupled to said inductive coil and said matching capacitor for rectifying said RF signal.

17. The implantable receiver circuit of claim 16, wherein the capacitor is selected to provide resonant operation of said implantable receiver circuit.

18. The implantable receiver circuit of claim 16, wherein said Class E full wave low dv/dt rectifier with input between nodes A and B and output between nodes E and F comprises:
   a first parallel capacitor coupled between nodes B and F;
   a second parallel capacitor coupled between nodes F and A;
   a first diode coupled between nodes B and F;
   a second diode coupled between nodes F and A;
   a first inductor coupled between nodes B and E;
   a second inductor coupled between nodes A and E; and
   a filter capacitor coupled across the output.

19. The implantable receiver circuit of claim 18, further comprising circuitry for synchronous rectification.

20. The implantable receiver circuit of claim 19, wherein said circuitry for synchronous rectification comprises:
   gate control circuitry for sensing current in said first diode and said second diode;
   a first transistor having a gate coupled to said gate control circuitry and having drain and source coupled in parallel with leads of said first diode;
   a second transistor having a gate coupled to said gate control circuitry and having drain and source coupled in parallel with leads of said second diode;
   wherein said gate control circuitry is adapted to turn on said first transistor when the current in said first diode is above a threshold level; and
   wherein said gate control circuitry is adapted to turn on said second transistor when the current in said second diode is above said threshold level.

* * * * *

UNITED STATES PATENT AND TRADEMARK OFFICE
CERTIFICATE OF CORRECTION

PATENT NO.   : 6,240,318 B1
DATED        : May 29, 2001
INVENTOR(S)  : Richard P. Phillips It is certified that error appears in the above-identified patent and that said Letters Patent is hereby corrected as shown below:

Column 4,
Line 45, insert a period after "invention"

Column 5,
Line 15, after "output" and before "the" insert -- of --

Column 6,
Line 15, change "$\theta_{link}$" to -- $\eta_{link}$ --

Column 7,
Lines 4 and 66, change "$\theta_{link}$" to -- $\eta_{link}$ --

Column 8,
Lines 6, 9 and 20, change "$\theta_{link}$" to -- $\eta_{link}$ --

Signed and Sealed this

Fifth Day of August, 2003

JAMES E. ROGAN
*Director of the United States Patent and Trademark Office*